United States Patent
Newkome et al.

(10) Patent No.: US 7,589,229 B2
(45) Date of Patent: *Sep. 15, 2009

(54) T-BUTYL CASCADE POLYMERS

(75) Inventors: George R. Newkome, Medina, OH (US); Charles N. Moorefield, Akron, OH (US); Rajani K. Behera, Orissa (IN)

(73) Assignee: The University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/698,422

(22) Filed: Jan. 26, 2007

(65) Prior Publication Data

US 2007/0142663 A1    Jun. 21, 2007

Related U.S. Application Data

(60) Division of application No. 10/462,397, filed on Jun. 16, 2003, now Pat. No. 7,183,426, which is a continuation of application No. 08/705,157, filed on Aug. 29, 1996, now abandoned, which is a continuation-in-part of application No. 08/477,912, filed on Jun. 7, 1995, now abandoned, which is a division of application No. 08/375,187, filed on Jan. 18, 1995, now abandoned, which is a continuation of application No. 08/267,500, filed on Jun. 29, 1994, now abandoned, which is a continuation of application No. 08/120,640, filed on Sep. 13, 1993, now abandoned, which is a continuation of application No. 07/871,403, filed on Apr. 21, 1992, now abandoned.

(51) Int. Cl.
*C07C 205/00* (2006.01)
(52) U.S. Cl. .................. 560/156; 560/171; 560/157
(58) Field of Classification Search .................. 560/156, 560/171, 157
See application file for complete search history.

(56) References Cited

OTHER PUBLICATIONS

G.R.Newkome, R.K.Behera, C.N.Moorefield, G.R.Baker,☐☐Cascade Polymers:Synthesis and Characterization of One-Dimentional Arborols Based on Adamantane,☐☐J.Org.Chem., 1991, 56, 7162-7167.*

* cited by examiner

*Primary Examiner*—Karl J Puttlitz
*Assistant Examiner*—Sudhakar Katakam
(74) *Attorney, Agent, or Firm*—Kohn and Associates PLL

(57) ABSTRACT

A method for forming cascade polymers specifically utilizing the amine monomer of the formula

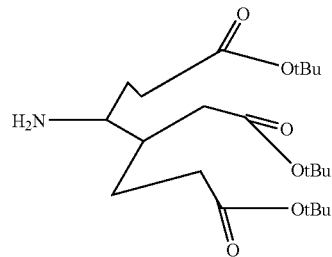

The monomer is made by initially reacting nitromethane and $CH_2$=$CHCO_2$— TBu by nucleophilic addition to form the triester nitrotrialkanoate of the formula

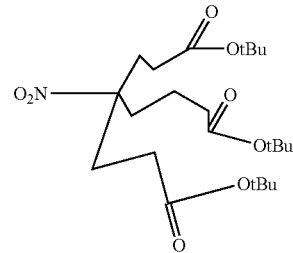

and then reducing the nitrosubstituent to afford the said amine monomer.

7 Claims, No Drawings

T-BUTYL CASCADE POLYMERS

CROSS-RELATED REFERENCE SECTION

This application is a Divisional application of U.S. patent application Ser. No. 10/462,397, filed Jun. 16, 2003 now U.S. Pat No. 7,183,426, which is a Continuation of U.S. patent application Ser. No. 08/705,157, filed Aug. 29, 1996, now abandoned, which is a CIP of U.S. patent application Ser. No. 08/477,912, filed Jun. 7, 1995, now abandoned, which is a Divisional of U.S. patent application Ser. No. 08/375,187, filed Jan. 18, 1995, now abandoned, which is a Continuation of U.S. application Ser. No. 08/267,500, filed Jun. 29, 1994, now abandoned, which is a Continuation of U.S. patent application Ser. No. 08/120,640, filed Sep. 13, 1993, now abandoned, which is a Continuation of U.S. patent application Ser. No. 07/871,403, filed Apr. 21, 1992, now abandoned, all of which are incorporated herein by reference.

TECHNICAL FIELD

The present invention relates to the field of polymer chemistry and, more specifically with regard to the field of cascade or dendritic polymer chemistry. These polymers are based upon the application of mathematical progressions to organic synthesis and thereby possess well-defined molecular topologies.

BACKGROUND OF THE INVENTION

The field of cascade polymer chemistry is expanding the traditional synthetic limits into the meso-macro-molecular frontier. Such polymers possess well-defined molecular topologies as they can be constructed in discrete layers rendering upon the molecule discrete, symmetric and consistent chemical characteristics.

These polymeric structures provide specific micellar molecules.

The synthesis and spectral features of cascade polymers, also referred to as arborols possessing two-, three- and four-directional microenvironments with functionalized polar outer surfaces, have been recently reported (1-8). Depending on their molecular shape, many of these macromolecules aggregate to form gels or show novel micellar characteristics in aqueous solution (3,7,8). In view of an interest in generating a spherical hydrophilic surface with a compact lipophilic core, the present invention provides a cascade system which in one embodiment emanates from a central adamantane core. This core includes bridgehead positions which have suitable geometry to mimic a tetrahedral nucleus and can be envisioned as an extended methane core. Such a core is an ideal starting point toward four-directional cascade polymers.

In constructing such spherical polymers, several further problems were uncovered. One such problem related to the generation of a tri-branched monomer which would not cyclize. More specifically, to provide tri-valent branching from a single branch of a polymer, at least two qualities are required. First, there must be directionality such that the monomer combines with the branch so as to expose three branch binding sites for further tiering of the macromolecule. The branches of the macromolecule extending from a central core must also extend sufficiently to be able to allow further reactions therewith for the additional tiering while not cyclizing onto themselves. Cyclizing removes branches from being chemically reactive thereby causing a dead-end to the tiering process. For example, the following reaction sequence generated the polymeric product set forth below.

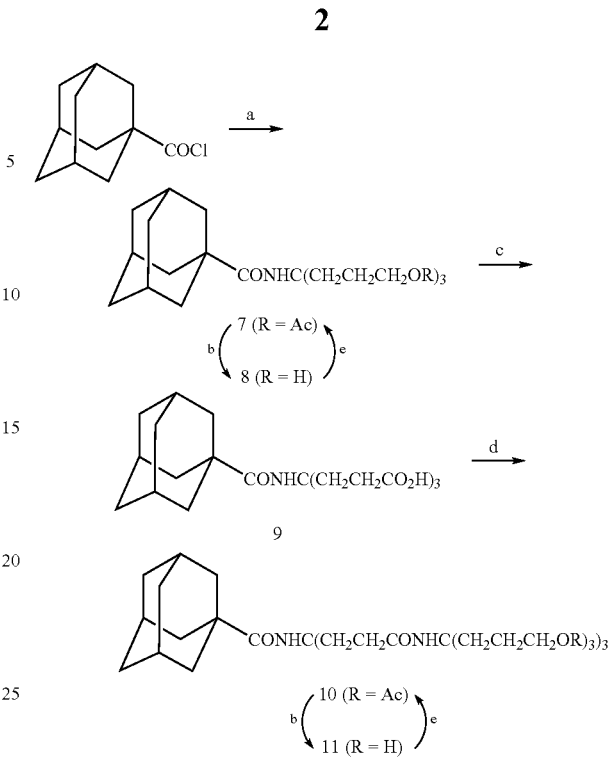

Attempted oxidation of compound 11 by a $RuO_2$ procedure of Irngartinger, et al. (9) resulted in limited success in that complete oxidation was not reproducible.

Applicant herein provides novel monomers which are ideal in that they do not cyclize and further can be used in a cascade system for producing macromolecular monomers through tetradirectional polymers, particularly on an adamantane, methane equivalent, or four-directional core.

Further, the present invention provides novel four-directional spherical dendritic macromolecules based on adamantane made in accordance with the novel method set forth herein.

SUMMARY OF THE INVENTION

In accordance with the present invention, there is a method forming an amine monomer of the formula

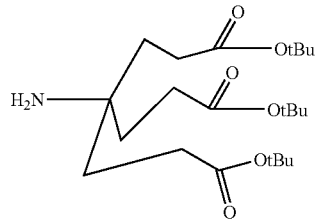

by the steps of reacting nitromethane and $CH_2\!\!=\!\!CHCO_2\text{-}TBu$ by nucleophilic addition to form the triester nitrotrialkanoate of the formula

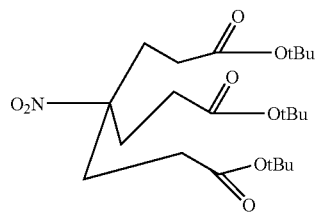

and reducing the nitrosubstituent to said amine monomer.

Further in accordance with the present invention the novel amine monomer can be used to create several novel one, two, three, or four-directional polymers based on the adamantane, or similar core.

DETAILED DESCRIPTION OF THE INVENTION

The present invention generally will provide a monomer of the formula

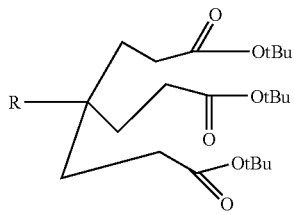

wherein R is selected from the group consisting essentially of $NH_2$ and $NO_2$. This novel compound is a building block for novel cascade polymers made in accordance with the inventive method set forth below. Products made in accordance with the present invention can be used in various fields, such as pharmaceutical chemistry, as micelles. However these compounds are used to make unimolecular micelles as opposed to multi-molecular micelles, previously known in the art.

These monomeric micelles generally have a core and branching which leads from the core. In accordance with the present invention, the branching can be tetra-directional extending from the four bridgehead positions of the core and can be tiered or layered such that a first layer of branching can be combined with the core and then subsequent layers can be added to provide a well-defined molecular topology.

More specifically, as discussed above, attempted oxidation of the arborol of the formula

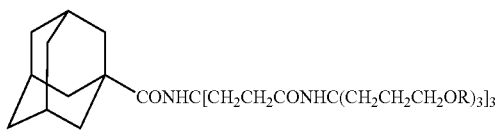

by the $RuO_2$ procedure discussed above met with limited success in that complete oxidation was not reproducible. To circumvent this problem as well as to shorten the overall iterative procedure, the novel building block di-tert-butyl 4-amino-[2-(tert-butoxycarbonylethyl]-heptanedioate was prepared by the following scheme.

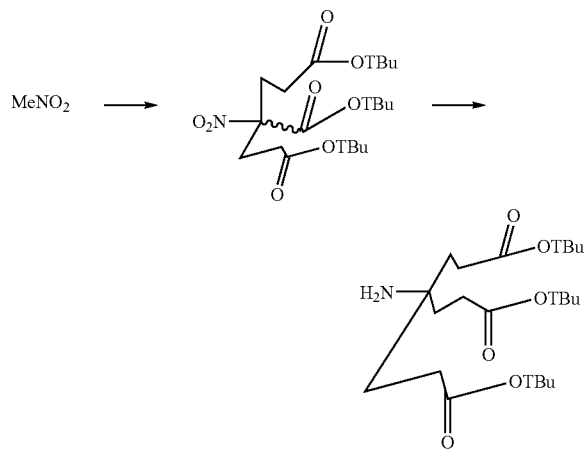

A key factor was the bulky nature of the tert-butyl ester, so it was necessary to prevent lactam formation during reduction of the nitro functionality. That is, the following reaction did not occur under the condition conducted in accordance with the present invention.

An attempt to synthesize the nitro ester precursor by modification of the procedure reported by Bruson and Riener(10) using tert-butyl acrylate in place of the acrylonitrile resulted in a poor yield of about 5%. To circumvent this sluggish nucleophilic addition, the reaction temperature was elevated during the initial addition phase and then maintained at about 70° to 80° C. for one hour. This modification resulted in a 72% yield of the desired triester, which was confirmed by $^{13}C$ NMR by the peaks for the quaternary and carbonyl carbons at 92.1 and 170.9 ppm, respectively. The $^1H$ NMR spectrum showed a singlet at 1.45 ppm assigned to $(CH_3)_3CO$ in a multiplet at 2.21 ppm for the methylene protons. Analysis of the crystal structure ultimately confirmed the analysis.

The prior art discusses diverse reduction conditions for the conversion of nitroalkanols to aminoalkanols(11). The use of platinum, palladium, or Raney nickel catalyst all resulted in very poor yields and gave mostly recovered nitrotrialkanoate compound. However, a reduction with specially generated T-1 Raney nickel by the process of Domingues, et al. (12) at elevated temperatures (ca. 60° C.) gave an 88% yield of the aminoester after purification. Successful reduction was confirmed by $^{13}C$ NMR by an upfield shift for the quaternary carbon at 52.2 ppm. The $^1H$ NMR spectrum of the aminotrialkanoate showed a singlet at 1.44 ppm for the tert-butyl group, multiplets at 1.68 and 2.26 ppm for the methylene protons and a broad singlet at 5.49 ppm for the amino moiety.

Since related alkyl esters of the aminotrialkanoate could not be prepared because of facile intramolecular lactam formation during the hydrogenation of the nitro moiety, the tert-butyl ester is ideal in that no cyclization was observed. The advantages of the tert-butyl ester are: a) reduced number of overall steps for cascade synthesis; b) easy preparation on a large scale; c) facile hydrolysis to the desired acids in nearly quantitative yield; and d) the poly tert-butyl esters were easily purifiable solids.

An example of the use of the tert-butyl ester in a cascade synthesis is as follows. Treatment of adamantanecarbonyl chloride with the aminotrialkanoate as set forth above furnished 71% yield of the desired triester (amine monomer) of the formula

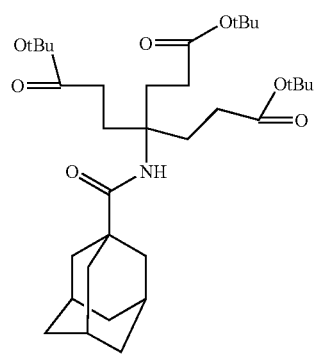

This structure was confirmed by $^{13}C$ NMR by the peaks at 172.8 (ester), 177.4 (CONH), and 56.7 ppm (side-quaternary carbon). Hydrolysis of the ester to a triacid was accomplished with about 100% yield by treatment with formic acid. It was identical in all respects to a sample prepared by the above procedure. Application of peptide coupling procedures known in the art of the acid with the aminotrialkanoate in the presence of DCC and 1-hydroxybenzotriazole in dry dimethyl formamide (DMF) afforded a 61% yield of a nonaester (13). The following scheme summarizes the reaction sequence

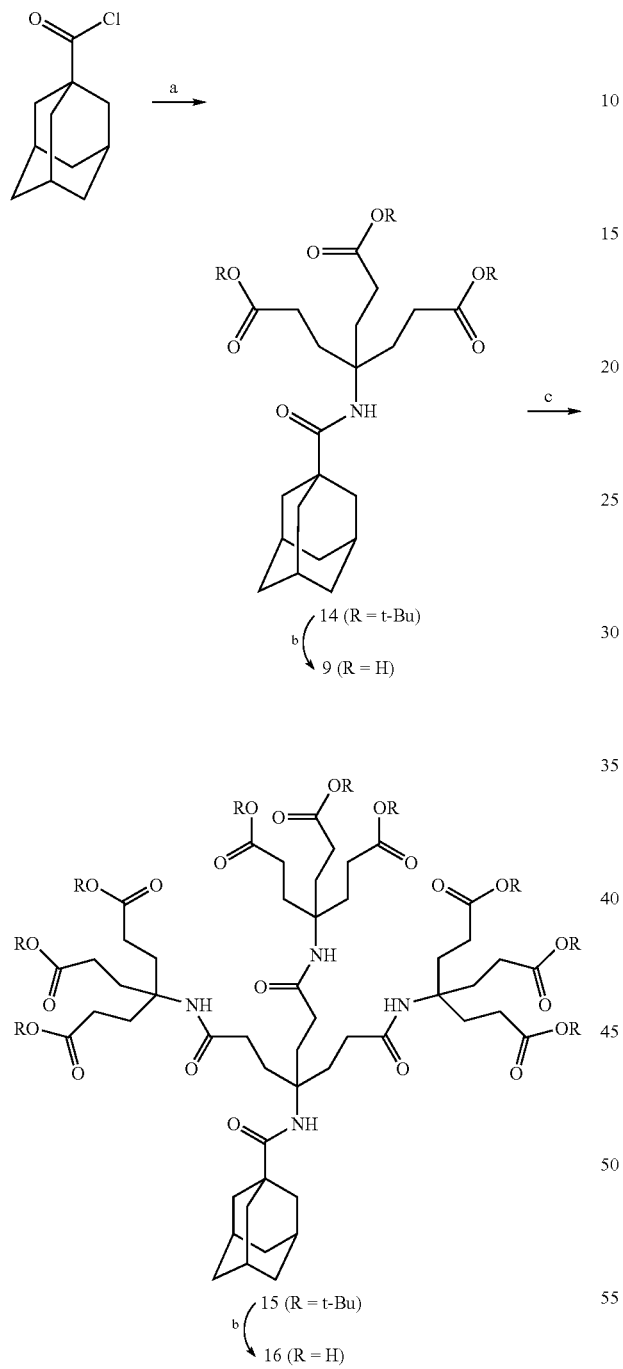

The presence of the structure was confirmed by $^{13}$C NMR showing two carbonyl peaks at 172.6 (ester) and 177.0 ppm (CONH) as well as the peaks for the side-chain quaternary carbons at 57.6 and 57.0 ppm thereby confirming the transformation. The specific assignment of internal and external methylene signals was based on the intensity ratios as well as the fine shape, the internal methylenes being broader. The final acid was obtained in a 95% yield by the treatment of the ester with formic acid. The absence of the tert-butyl groups in the NMR spectra and the shift for the carbonyl, 172.6 ppm (ester) to 177.6 ppm (acid) supports the conclusion that hydrolysis occurred.

A large scale preparation of the nitrotriester and its subsequent reduction to the amine has been developed. Specifically, the nitrotriester 1 was prepared via treatment of nitromethane with slightly more than three equivalents of tert-butyl acrylate in dimethoxyethane (DME). Trace yellow impurities produced in the reaction were easily removed by recrystallization. Removal of these colored contaminants circumvents chromatographic purification of the desired monomer 2.

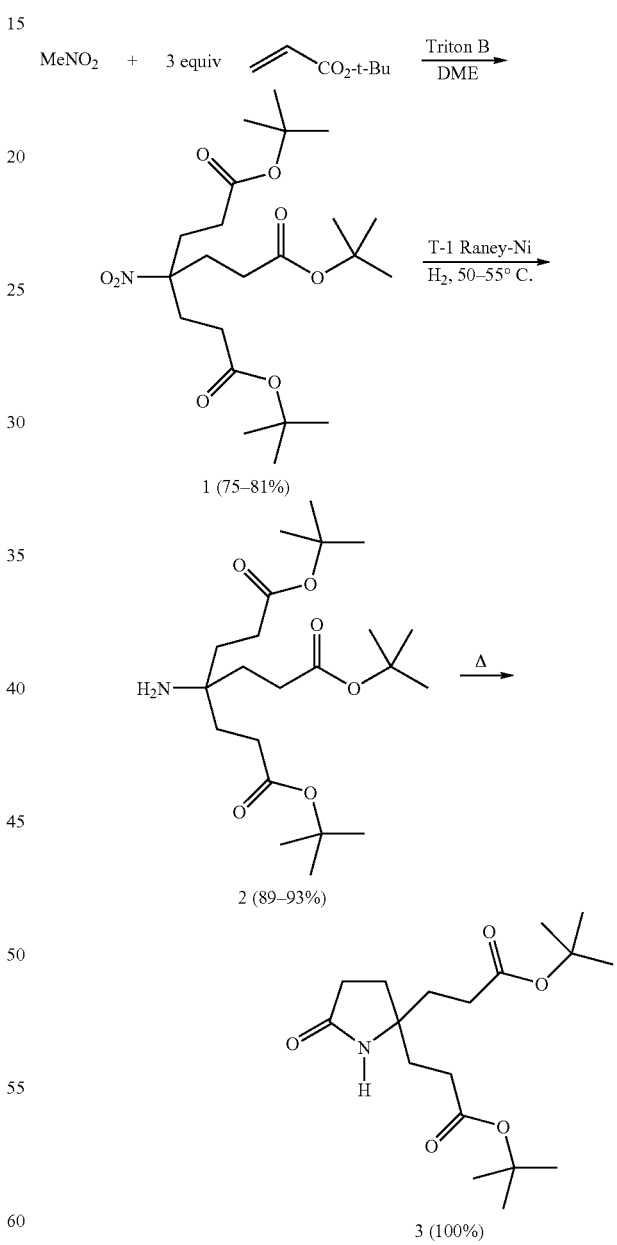

Hydrogenation of the nitrotriester 1 to the aminotriester 2 at slightly elevated temperature presented a serendipitous exception to the reduction products of known tertiary, γ-nitroester (Weis et al., 1995). All previously known examples of such reductions readily cyclize to afford the corresponding 2,2'-disubstituted pyrrolidones. Therefore, catalytic hydrogenation conducted under carefully controlled temperature conditions using freshly prepared T-1 Raney Nickel at 45-55° C. provided (ca. 90%) the pure monomer 2.

The crystalline amine 2 is stable for prolonged periods when stored at ≦15° C., however the presence of solvent or extended storage at 25° C. can result in the formation (about 5-7% over several months) of di-tert-butyl 5-oxo-2,2-pyrrolidinedipropionate (3) (Young, 1993). Attempts to recrystallize 2 were initially frustrated by the thermal cyclization at elevated temperatures, which further dictated that in vacuo solvent removal be performed below 50° C. Subsequently, it has been determined that aminoester 2 can be cyclized quantitatively in the solid state at 105-110° C.; while in solution, cyclization occurs at 65-80° C.

Experimental Section

General Comments. Melting point data were obtained in capillary tubes with a Gallenkamp melting point apparatus and are uncorrected. $^1$H and $^{13}$C NMR spectra were obtained in $CHCl^3$, except where noted, with $Me_4Si$ as the internal standard (δ=0 ppm), and recorded at either 80 or 360 MHz. Infrared spectral data were obtained on an IBM –38 spectrometer. Elemental analyses were performed by MicAnal Laboratories in Tucson, Ariz.

Di-tert-butyl 4-Nitro-4-[2-tertbutoxycarbonyl)ethyl]heptanedioate. A stirred solution of $MeNO_2$ (6.1 g, 100 mmol), Triton B (benzyltrimethylammonium hydroxide, 50% in MeOH; heated to 65° to 70° C. tert-Butyl acrylate (39.7 g, 310 mmol) was added portion wise to maintain the temperature at 70° to 80° C. Additional Titon B (2×1 mL) was added when the temperature started to decrease; when the addition was completed, the mixture was maintained at 70° to 75° C. for one hour. After concentration in vacuo, the residue was dissolved in $CHCl_3$ (200 mL), washed with 10% aqueous HCl (50 mL) and brine (3×50 mL), and dried $MgSO_4$). Removal of solvent in vacuo gave a pale yellow solid, which was crystallized (95% EtOH) to solid, which was crystallized (95% EtOH) to afford a 72% yield of the triester, as white microcrystals: 33 g; mp 98-100° C.; $^1$H NMR δ 1.45 (s, $CH_3$, 27 H), 2.21 (m, $CH_2$, 12 H); $^{13}$C NMR δ 27.9 ($CH_3$, 29.7 $CH_2CO$), 30.2 ($CCH_2$), 80.9 $CCH_3$), 92.1 ($O_2NC$), 170.9 (CO); IR (KBr) 1542 ($NO_2$), 1740 (CO) cm$^{-1}$. Anal. Calcd. for $C_{22}H_{39}O^8N$: C, 59.35; H, 8.76; N, 3.14. Found: C, 59.27; H, 9.00; N, 3.14.

Di-tert-butyl 4-Amino-4-[2-(tert-butoxycarbonyl)ethyl]heptanedioate. A solution of the above synthesized nitro triester (4.46 g, 10 mmol) in absolute EtOH (100 mL) with T-1 Raney $Ni_{12}$ (4.0 g) was hydrogenated at 50 psi and 60° C. for 24 hours. The catalyst was cautiously filtered through Celite. The solvent was removed in vacuo, affording a viscous liquid, which was column chromatographed ($SiO_2$), eluting with EtOAc to give a 88% yield of the amino triester as a white crystalline solid: 3.7 g; mp 50-52° C.; $^1$H NMR δ 1.44 (s, $CH_3$, 27 H), 1.78 (m, $CH_2$, 12 H); $^{13}$C NMR δ 27.8 ($CH_3$), 29.8 ($CH_2CO$), 34.2 ($CCH_2$), 52.2 ($H_2NC$), 80.0 ($CCH_3$), 172.8 (CO); IR (KBr) 1745 (CO) cm$^{-1}$. Anal. Calcd. for $C_{22}H_{41}O_6N$: C, 63.58; H, 9.95; N, 3.37. Found: C, 63.72; H, 10.05; N, 3.38.

1-[[N-[3-(tert-Butoxycarbonyl)-1,1-bis[2-tertbutoxycarbonyl)ethyl]propyl]amino]carbonyl]adamatane. A solution of 1-adamantanecarbonyl chloride (1 g, 5 mmol), amine monomer (2.1 g, 5 mmol), and $Et_3N$ (600 mg, 6 mmol) in dry benzene (25 mL) was stirred at 25° C. for 20 hours. The mixture was washed sequentially with aqueous $NaHCO_3$ (10%), water, cold aqueous HCl (10%), and brine. The organic layer was dried ($Na_2SO_4$) and then concentrated in vacuo to give residue which was chromatographed ($SiO_2$), eluting first with $CH_2Cl_2$ to remove some by-products and then with EtOAc to give a 71% yield of the ester as a white solid: 2 g; mp 84-86° C.; $^1$H NMR δ 1.46 (s, $CH_3$, 27 H), 1.68-2.1 (m, CH, $CH_2$, 27 H), 4.98 (bs, NH, 1 H); $^{13}$C NMR δ 28.0 ($CH_3$), 28.2 (γ-CH), 29.8, 30.1 ($NHCCH_2CH_2CO$), 36.4 (δ-$CH_2$), 39.2 (β-$CH_2$), 41.2 (α-C), 56.7 (NHC), 80.5 ($CCH_3$), 172.8 (COO), 177.4 (CONH); IR (KBr) 3350, 2934, 2846, 1740, 1638, 1255k 1038 cm$^{-1}$, Anal. Calcd. for $C_{33}H_{55}O_7N$: C, 68.58; H, 9.60; N, 2.43. Found: C, 68.36; H, 9.66; N, 2.36.

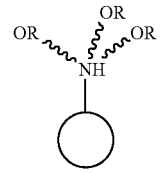

1-[[N-]3-[[N-[3-(tert-Butoxycarbonyl)-1,1-bis[2-(tert-butoxycarbonyl)ethyl]propyl]-amino]carbonyl]-1,1-bis[2-[[N-[3-(tert-buxtoxycarbonyl)-1,1-bis[2-(tert-buxtoxycarbonyl)-ethyl]propyl]amino]carbonyl]ethyl]propyl]amino]carbonyl] adamatane. A mixture of the triacid 1-[[N-[3-carboxyl-1,1-bix(2-carboxyethyl)propyl]-amino]carbonyl]adamantane (400 mg, 1 mmol) amine monomer (1.45 g, 3.5 mmol), DCC (620 mg, 3 mmol), and 1-hydroxybenzotriazole (400 mg, 3 mmol) in dry DMF (15 ml) was stirred at 25° C. for 48 hours. After filtration of the dicyclohexylurea, the solvent was removed in vacuo. The residue was dissolved in $CH_2Cl_2$ (50 mL) and sequentially washed with cold aqueous HCl (10%), water, aqueous $NaHCO_3$ (10%), and brine. The organic phase was dried ($Na_2SO_4$). Removal of solvent in vacuo gave a thick viscous residue, which was flash chromatographed ($SiO_2$) eluting first with $EtOAc/CH_2Cl_2$ (1:1) then with 5% MeOH in EtOAc, furnished A 61% yield of the ester, as a white solid: 970 mg; mp 115-118° C.; $^1$H NMR δ 1.42 (s, $CH_3$, 81 H), 1.64-2.20 (m, CH, $CH_2$, 63 H), 5.58 (bs, NH, 4H) $^{13}$C NMR δ 27.9 ($CH_3$), 28.4 (γ-CH), 29.6, 30.0 ($NHCCH_2CH_2COO$), 31.6, 32.2 ($NHCCH_2CH_2CONH$), 36.6 (γ-$CH_2$), 39.2 (β-$CH_2$), 41.1 (α-C), 57.0 ($NHCCH_2CH_2COO$), 57.6 ($NHCCH_2CH_2CONH$), 80.3 $CCH_3$), 172.6 (COO), 177.0 (CONH); IR (KBr) 3348, 2936, 2850, 1740, 1665, 1260, 1040 cm$^{-1}$. Anal. Calcd. for $C_{87}H_{148}O_{22}N_4$: C, 65.22; H, 9.31; N, 3.50. Found: C, 65.41; H, 9.30; N, 3.39.

1-[[N-[3-[[N-[3-Carboxy-1,1-bis(2-carboxyethyl)propyl] amino]carbonyl]-1,1-bix[2-[[N-[3-carboxy-1,1-bix(2-carboxyethyl)propyl]-amino]carbonyl]ethyl]propyl]amino]carbonyl]-adamantane. A solution of the above tert-butyl ester (800 mg, 500 μmol) in formic acid (96%, 5 mL) was stirred at 25° C. for 12 hours. The solvent was removed in vacuo to give a residue; toluene (5 mL) was added and the solution was again evaporated in vacuo to azeotropically remove residual traces of formic acid. The resulting white solid was extracted with warm acetone (5×50 mL). The combined extract was filtered ($SiO_2$), eluting with acetone. The residue obtained after concentration was dissolved in aqueous NaOH (10%) and acidified with concentration HCl to give 95% yield of the acid as a white solid: 520 mg, mp 346° C. dec; $^1$H NMR ($Me_2SO$-$d_6$) δ 1.82-2.40 (m, CH, $CH_2$, 63 H), 4.45 (bs, OH, 9 H, exchanged with $D_2O$), 6.28 (bs, NH, 4H); $^{13}$C NMR ($Me_2SO$-$d_6$) δ 29.6 (γ-CH), 30.2 ($NHCCH_2CH_2COOH$), 31.0, 32.4 ($NHCCH_2CH_2CONH$), 37.8 (δ-$CH_2$), 40.1 (β-$CH_2$), 42.5 (α-C), 58.0 ($NHCCH_2CH_2CONH$), 58.4 ($NHCCH_2CH_2COOH$), 177.6 (COOH), 179.8 (CONH); IR (KBr) 3360, 3340-2600, 2900, 1744, 1690, 1245, 1090 cm$^{-1}$. Anal. Calcd. for $C_{51}H_{76}O_{22}N_4$: C, 55.83; H, 6.98; N, 5.11. Found: C, 55.71; H, 7.04; N, 4.98.

The monomers of the present invention can be used for the design and synthesis of novel dendritic polymers which are one, two, three, or four-directional. In accordance with the present invention, the monomers can be used to synthesize four-directional spherical dendritic macromolecules based on adamantane. The use of the aminotrialkanoate monomer offers several advantages. The t-butyl ester intermediates are easily purified solids. Further, only two steps are required to progress from generation to generation.

A specific example of a synthesis is as follows. An acid chloride of the following formula

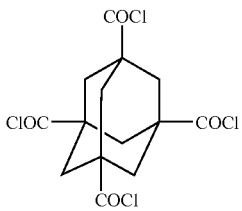

is treated with the aminotrialkanoatee present invention to afford a dodecaester of the following formula

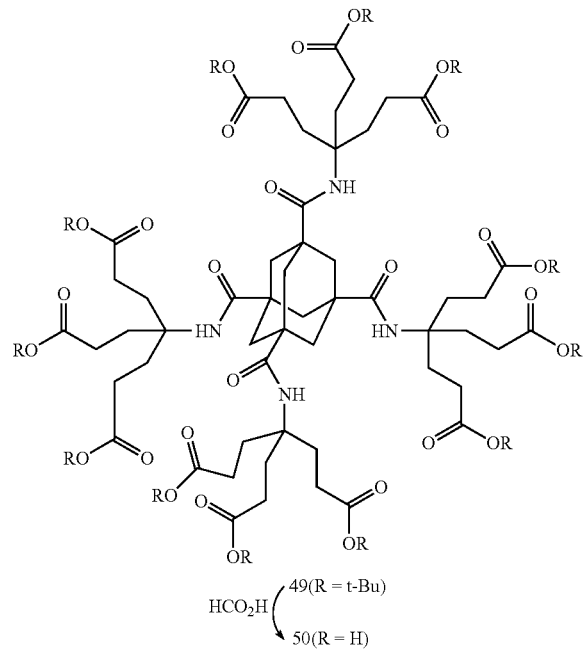

wherein R=t-Bu.

The dodecaester was hydrolyzed in good yield with 96% formic acid to yield the corresponding dodecaacid.

Addition of further tiers was easily obtained by the coupling of the dodecaacid and further layers of the aminotrialkanoate with DCC an 1-HBT to afford the ester wherein R=TBU. Upon hydrolysis, the ester quantitatively generated the corresponding next tiered polyacid.

A specific example of the method of forming the above-mentioned acid moiety is as follows.

1,3,5,7-Tetrakis{[N-[3-(tert-butoxycarbonyl)-1,1-bis[2-(tert-butoxycarbonyl)ethyl]propyl]amino]carbonyl}-adamantane. A mixture of adamantanetetra-carboxylic acid (78 mg, 250 μmol) and freshly distilled $SOCl_2$ (2 mL) was refluxed for 4 hours. Excess of $SOCl_2$ was removed in vacuo, benzene (5 mL) was added, and the solution was concentrated in vacuo to yield the corresponding tetraacyl chloride, as a white solid.

Crude 1,3,5,7-Tetrakis(chlorocarbonyl) adamantane, amine monomer (450 mg, 1.1 mmol), and $Et_3N$ (110 mg, 1.1 mmol) in dry benzene (10 mL) were stirred at 25° C. for 20 hours. Additional benzene (40 mL) was added, and the mixture was sequentially washed with aqueous $NaHCO_3$ (10%), water, cold aqueous HCl (10%), and brine. The organic phase was dried ($Na_2SO_4$) and then concentrated in vacuo to furnish a viscous oil, which was chromatographed ($SiO_2$), eluting with 5% MeOH in EtOAc to generate a 61% yield of the dodecaester, as a white solid: 290 mg; mp 105-107° C.; $^1$H NMR δ 1.40 (s, $CH_3$, 108 H), 172 (s, $CH_2$, 12 H), 2.24 (m, $CH_2$, 48 H), 5.88 (bs, NH 4 H); $^{13}$C NMR δ 28.1 ($CH_3$), 30.0, 30.4 ($CCH_2CH_2COO$), 39.0 (β-$CH_2$), 42.8 (α-C), 57.1 (HNC), 80.2 ($CCH_3$), 173.1 (COO), 177.6 (CONH); IR (KBr) 3348, 2930, 2845, 1740, 1645, 1260, 1038 cm$^{-1}$. Anal. Calcd. for $C_{102}H_{172}O_{28}N_4$: C, 64.38; H, 9.12; N, 2.95. Found: C, 64.52; H, 8.91; N, 2.86.

1,3,5,7-Tetrakis{[N-[3-carboxy-1,1-bis(2-carboxyethyl)propyl]amino]carbonyl}-adamantane. A solution of the dodecaester (190 mg, 100 μmol) in formic acid (96%, 2 mL) was stirred at 25° C. for 20 hours. Excess solvent was removed in vacuo, and toluene (3×2 mL) was added. The solvents were removed in vacuo to give a 94% yield of the dodecaacid, as a white solid: 115 mg; mp 282-284° C. dec; $^1$H NMR ($D_2O$) δ 1.84 (s, $CH_2$, 12H), 2.34 (m, $CH_2$, 48H); $^{13}$C NMR ($D_2O$) δ 30.1 ($CCH_2CH_2COOH$), 38.8 (β-$CH_2$), 42.7 (α-C), 58.6 (HNC), 177.8 (COOH), 180.4 (CONH); (KBr) 3360, 3330-2600, 2903, 1745, 1690, 1245, 1090 cm$^{-1}$. Anal. Calcd. for $C_{54}H_{76}O_{28}N_4$: C, 52.75; H, 6.23; N, 4.56. Found: C, 52.59; H, 6.22; N, 4.51.

1,3,5,7-Tetrakis{[N-[3-[[N-[3-(tert-butoxycarbonyl)-1,1-bis[2-(tert-butoxycarbonyl)-ethyl]propyl]amino]carbonyl]-1,1-bis[2-[[N-[3-(tert-butoxycarbonyl)-1,1-bis[2-(tert-butoxycarbonyl)ethyl]propyl]amino]carbonyl]-ethyl]propyl]amino]carbonyl}adamantane. A mixture of the dodecaacid (74 mg, 60 μmol), the amine monomer (330 mg, 790 μmol), dicyclohexyl-carbodiimide (DCC; 150 mg, 720 μmol), and 1-hydroxybenzotriazole (100 mg, 740 μmol) in dry DMF (3 mL) was stirred at 25° C. for 48 hours. After filtration of dicyclohexylurea, the solvent was removed in vacuo to give a residue, which was dissolved in EtOAc (25 mL) and was sequentially washed with cold aqueous HCl (10%), water, aqueous $NaHCO_3$ (10%), and brine. The organic phase was dried ($Na_2SO_4$) and concentrated in vacuo, and the residue was chromatographed ($SiO_2$), eluting first with EtOAc/$CH_2Cl_2$ (1:1) to remove some impurities and then with 5% MeOH in EtOAc to furnish a 58% yield of the ester, as a white solid: 200 mg; mp 138° C.; $^1$H NMR δ 1.40 (s, $CH_3$); $^{13}$C NMR δ 28.1 ($CH_3$), 30.0 ($CCH_2CH_2CONH$), 29.8, 30.2 ($CCH_2CH_2COO$), 38.9 (β-$CH_2$), 42.4 (α-C), 57.2 ($CCH_2CH_2COO$), 57.6 ($CCH_2CH_2CONH$), 80.0 ($CCH_3$), 172.8 (COO), 177.8 (CONH); IR (KBr) 3350, 2938, 2846, 1740, 1680, 1260, 1045 cm$^{-1}$. Anal. Calcd for $C_{318}H_{544}O_{88}N_{16}$: C, 63.64; H, 9.14; N, 3.74. Found: C, 63.28; H, 8.96; N, 3.77.

1,3,5,7-Tetrakis{[N-[3-[[N-[3-carboxy-1,1-bis(2-carboxyethyl)propyl]amino]carbonyl]-1,1-bis[2-[[N-[3-carboxy-1,1-bis(2-carboxyethyl)-propyl]amino]carbonyl]ethyl]propyl]amino]-carbonyl}adamantane. A solution of the ester (150 mg, 25 μmol) in formic acid (96%, 2 mL) was stirred at 25° C. for 20 hours. Workup and purification, similar to that of the dodecaacid, gave (95%) the corresponding acid, as a very hygroscopic solid: mp 350-354° C. dec; $^1$H NMR ($D_2O$) δ 1.80 (s, $CH_2$, 12 H), 2.18-2.41 (m, $CH_2$, 192 H) $^{13}$C NMR ($D_2O$) δ 30.2 ($CCH_2CH_2COOH$), 30.8, 31.6 ($CCH_2CH_2CONH$), 39.1 (β-$CH_2$), 42.8 (α-C), 58.1 ($CCH_2CH_2CONH$), 58.5 ($CCH_2CH_2COOH$), 178.0 (COOH), 180.2 (CONH); IR (KBr) 3360, 3340-2600, 2920, 1745, 1685, 1240, 1060 cm$^{-1}$.

Large Scale Preparation of Di-tert-butyl 4-[2-(tert-butoxycarbonyl)ethyl]-4-nitroheptane-dicarboxylate (1). A 5-liter 3-necked flask, equipped with a 500 mL addition funnel, a thermometer, a reflux condenser and a 2-inch magnetic stirring bar was charged with 1,2-dimethoxyethane (DME, 500 mL) and $MeNO_2$ (122 g, 108.3 mL, 2 mol). The solution was heated to 65-70° C., and Triton-B (20 mL, 40% in MeOH) was added. Tert-butyl acrylate (794 g, 908 mL, 6.20 mol) was added at such a rate to maintain a temperature of 75-85° C. The addition was completed within 2 to 2.5 hours. When the temperature was maintained at 70-80° C. for two hours, the solution was decanted from insoluble polymeric material (which adheres to the wall of the flask) and concentrated in vacuo. The resulting light yellow residue was dissolved in ether (2.5 L), washed with ice cold 10% aqueous HCl (2×200 mL), an aqueous saturated $NaHCO_3$ (2×200 mL), and water (2×200 mL), then dried and clarified [$Na_2SO_4$ (100 g) with celite (10 g)]. The ether was removed in vacuo to give a solid mass, which was dissolved in warm ethanol (ca. 1.3 L). The solution was allowed to cool and maintained at 0° C. for 24 hours. The resultant colorless crystals, were collected, washed with precooled methanol (500-600 mL) to remove any residual colored impurities, and dried in vacuo to afford 668-721 g (75-81%) of the white crystalline 1; mp 99-100° C., lit (Newkome et al., 1991) mp 98-100° C. $^1$H NMR: δ 1.45 (s, $CH_3$, 27H), 2.21 (m, $CH_3$, 27H), 2.21 (m, $CH_2$, 12H); $^{13}$C NMR: δ 27.9 ($CH_3$), 29.7 ($CH_2CO$), 30.2 ($CCH_2$), 80.9 ($CCH_3$), 92.1 ($CNO_2$), 170.9 ($CO_2$).

Di-tert-butyl 4-[2[(tert-butoxycarbonyl)ethyl]-4-aminoheptanedicarboxylate (2)

A. Preparation of T-1 Raney Nickel Catalyst (Dominguez et al., 1961). Caution should be maintained as this catalyst is easily handled when wet; however, it is extremely pyrophoric when dried and exposed to air. To 705 mL of water in a 2 L beaker rapidly stirred using a 2-inch magnetic stirring bar was added NaOH pellets (75 g). After dissolution, aluminum nickel alloy [30 g, Aldrich Chemical Co. (22,165-1), Raney R-type alloy] was added in one portion to the hot solution. There was a vigorous evolution of hydrogen and the temperature rose to ca. 85-90° C.; stirring was continued for one hour. The beaker was covered with a watch glass, and the supernatant alkaline solution was carefully decanted from the black catalyst. Distilled water (300-400 mL) was added, stirred for one to two minutes, and then decanted. This procedure was repeated four times. The catalyst was transferred into a 250 mL beaker and washed with absolute ethanol (5×150-200 mL); each time the catalyst was allowed to settle before the supernatant ethanol was decanted. The moist catalyst was used immediately.

B. Reduction Procedure. To a Parr hydrogenation bottle was added ethanol (25 mL), followed by the above freshly prepared catalyst [which should be covered (50-100 mL) with ethanol to ca. 75% of the total flash volume. The hydrogenation was performed at an initial pressure of 60 psi at 50-55° C., and generally required 45-75 minutes. Nitrotirester 1 is quite insoluble in ethanol while amine 2 is soluble. External cooling may be necessary so that the temperature does not exceed 55° C. The catalyst was removed by filtration through a sintered glass funnel, then washed with ethanol (50-80 ml) (Catalyst Destruction). If there are traces of catalyst in the filtrate, filtration must be repeated. The solvent was removed in vacuo (0.1 mm) to yield an oil, which was transferred to a crystallizing dish and allowed to solidify in vacuo to give 41.5-44.1 g (89-93%) of 2 as a white crystalline mass, mp 51° C., lit. (Newkome et al., 1991) mp 51-52° C. $^1$H NMR: δ 1.44 (s, $CH_3$, 27 H), 1.78 (m, $CH_2$, 12H); $^{13}$C NMR: δ 27.8 ($CH_3$), 29.8 ($CH_2CO$), 34.2 ($CCH_2$), 52.2 ($CNH_2$), 80.0 ($CCH_3$), 172.8 ($CO_2$); MS m/e 415.4 ($M^+$+1, 20).

Amine 2 can be cyclized upon heating to 110° C. for 48 hours to yield (100%) lactam 3, mp 132-133° C., lit. (Young, 1993) mp 131-132° C. $^1$H NMR: δ 1.44 (s, $CH_3$, 18 H), 1.83 (t, J=7.2 Hz, $CH_2CO$, 4H), 1.92 (t, J=8.0 Hz, $CH_2CONH$, 2H), 2.26 (t, J=7.2 Hz, $CCH_2$, 4H), 2.38 (5, J=8.0 Hz, $CCH_2CH_2CONH$, 2H), 6.92 (s, NH, 1H); $^{13}$C NMR: δ 27.9 ($CH_3$), 30.1 ($CH_2O$), 30.2, 30.25 [$CH_2CH_2$ (ring)], 34.6 ($CH_2CH_2CO_2$), 60.6 (HNC), 80.6 ($CO_2C$), 172.3 ($CO_2$), 177.2 (CONH); IR 1723, 1707 (C=O cm$^{-1}$. Anal. Calcd. for $C_{18}H_{31}NO_5$; C, 63.32; H, 9.15; N, 4.10. Found: C, 63.52; H, 9.25; N, 4.28.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES

1. Newkome, G. R.; Yao, Z.-q.; Baker, G. R.; Gupta, V. K. *J. Org. Chem.* 1985, 50, 2003.
2. Newkome, G. R.; Baker, G. R.; Saunders, M. J.; Russo, P. S.; Gupta, V. K.; Yao, Z.-q. Y.; Miller, J. E.; Bouillion, K. *J. Chem. Soc., Chem. Commun.* 1986, 752.
3. Newkome, G. R.; Baker, G. R.; Aria, S.; Saunders, M. J.; Russo, P. S.; Theriot, K. J.; Moorefield, C. N.; Rogers, L. E.; Miller, J. E.; Lieux, T. R.; Murray, M. E.; Phillips, B.; Pascal, L. *J. Am. Chem. Soc.* 1990, 112, 8458.
4. Newkome, G. R.; Yao, Z.-q.; Baker, G. R.; Gupta, V. K.; Russo, P. S.; Saunders, M. J.; *J. Am. Chem. Soc.* 1986, 108, 849.
5. Newkome, G. R.; Hu, Y.; Saunders, M. J.; Fronczek, F. R. *Tetrahedron Lett.* 1991, 32, 1133.
6. Newkome, G. R.; Moorefield, C. N.; Baker, G. R.; Johnson, A. J.; Behera, R. K. *Angew. Chem.* 1991, 103, 1205; *Angew. Chem., Int. Ed. Engl.* 1991, 30, 1176.
7. Newkome, G. R.; Moorefield, C. N.; Baker, G. R.; Saunders, M. J.; Grossman, S. H. *Angew. Chem.* 1991, 103, 1207; *Angew. Chem., Int. Ed. Engl.* 1991, 30, 1178.
8. Newkome, G. R.; Lin, X. *Macromolecules* 1991, 24, 1443.
9. Ingartinger, H.; Reimann, W. *J. Org. Chem.* 1988, 53, 3046.
10. Bruson, H. A.; Riener, T. W. *J. Amer. Chem. Soc.* 1943, 65, 23.
11. Gakenheimer, W. C.; Hartung, W. H. *J. Org. Chem.* 1944, 9, 85. Noland, W. E.; Kneller, J. F.; Rice, D. E. *Ibid.* 1957, 22, 695. Fanta, P. E.; Smat, R. J.; Piecz, L. F.; Clemens, L. *Ibid.* 1966, 31, 3113. Controulis, J.; Rebstock, M. C.; Crooks, H. M., Jr. *J. Am. Chem. Soc.* 1949, 71, 2463. Wheatly, W. B. *Ibid.* 1954, 76, 2832. Newman, M. S.;

Edwards, W. M. *Ibid.* 1954, 76, 1840. Herz, W.; Tocker, S. *Ibid.* 1955, 77, 3554. Baer, H. H.; Fischer, H. O. L. *Ibid.* 1960, 82, 3709.
12. Domingues, X. A.; Lopez, I. C.; Franco, R. *J. Org. Chem.* 1961, 26, 1625.
13. Bodanszky, M.; Bodanszky, A. The Practice of Peptide Synthesis in *Reactivity and Structure Concepts in Organic Chemistry*; 1984; Vol. 21, p. 145.
14. C. D. Weis and G. R. Newkome, *Synthesis,* 1053 (1995).
15. J. K. Young, Ph. D. (USF) Dissertation, 1993.
16. G. R. Newkome, R. K. Behera, C. N. Moorefield, G. R. Baker, *J. Org. Chem.,* [56], 7162 (1991).
17. Catalyst destruction following the hydrogenation can be effected by direct addition of the moist material to a 5%. aqueous HCl solution.

What is claimed is:

1. A method of forming an amine monomer of the formula

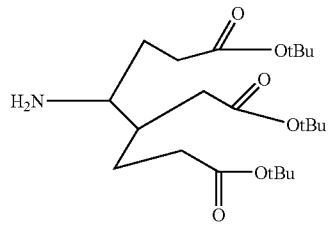

by the steps of reacting nitromethane and $CH_2$=$CHCO_2$-TBu by nucleophilic addition to form the triester nitrotrialkanoate of the formula

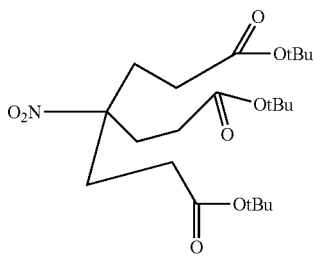

and reducing the nitrotrialkanoate to said amine monomer.

2. A method as set forth in claim 1 wherein said reacting step is further defined as reacting said methyl nitromethane and $CH_2$=$CHCO_2$-TBu in the presence of dimethoxyethane and Triton-B at a temperature of about 70° to 80° C. for about one hour.

3. A method as set forth in claim 1 wherein said reducing step is further defined as reducing the nitrotrialkanoate to the amine monomer with T-1 Raney nickel at a temperature of about 60° C.

4. A method of forming an amine monomer of the formula

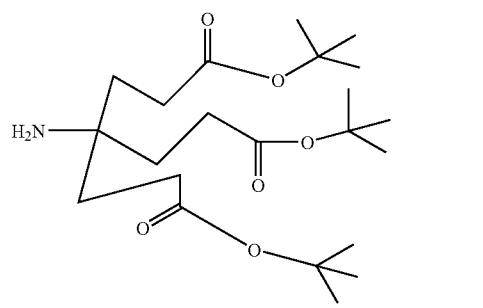

by the steps of (a) treating nitromethane with tert-butyl acrylate to form a nitrotriester of the formula

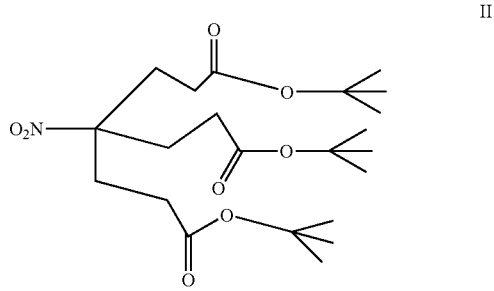

(b) recrystallizing the nitrotriester to remove impurities; and (c) hydrogenating the nitrotriester (II) to the aminotriester (I).

5. A method as set forth in claim 4 wherein said treating step is further defined as treating the nitromethane with greater than three equivalents of the tert-butyl acrylate in dimethoxyethane.

6. A method as set forth in claim 4 wherein said hydrogenating step is conducted using T-1 Raney Nickel at 45 to 55° C.

7. A method as set forth in claim 4 wherein the hydrogenating step is followed by removing solvent in vacuo below 50° C.

* * * * *